United States Patent
Mangiardi

(10) Patent No.: US 10,201,440 B2
(45) Date of Patent: Feb. 12, 2019

(54) STENT

(71) Applicant: Q3 MEDICAL DEVICES LIMITED, Dublin (IE)

(72) Inventor: Eric K. Mangiardi, Charlotte, NC (US)

(73) Assignee: Q3 MEDICAL DEVICES LIMITED, Dublin (IE)

( * ) Notice: Subject to any disclaimer, the term of this patent is extended or adjusted under 35 U.S.C. 154(b) by 139 days.

(21) Appl. No.: 14/841,196

(22) Filed: Aug. 31, 2015

(65) Prior Publication Data

US 2015/0366681 A1 Dec. 24, 2015

Related U.S. Application Data

(63) Continuation of application No. 12/539,314, filed on Aug. 11, 2009, now abandoned, which is a
(Continued)

(51) Int. Cl.
*A61F 2/04* (2013.01)
*A61F 2/844* (2013.01)
(Continued)

(52) U.S. Cl.
CPC .......... *A61F 2/844* (2013.01); *A61B 17/7233* (2013.01); *A61B 17/7258* (2013.01); *A61B 17/7283* (2013.01); *A61F 2/82* (2013.01); *A61B 17/7266* (2013.01); *A61B 17/7291* (2013.01); *A61F 2/06* (2013.01);
(Continued)

(58) Field of Classification Search
CPC .... A61F 2/915; A61F 2230/0069; A61F 2/07; A61F 2230/0067; A61F 2/89; A61F 2/86; A61F 2002/823; A61F 2002/072; A61F 2002/821
See application file for complete search history.

(56) References Cited

U.S. PATENT DOCUMENTS 4,642,104 A 2/1987 Sakamoto et al.
5,129,910 A * 7/1992 Phan ................ A61B 17/22031
604/264
(Continued)

FOREIGN PATENT DOCUMENTS

WO 99/09911 3/1999

OTHER PUBLICATIONS

European Search Report issued in European Patent Application No. 09842845.1 dated Feb. 18, 2015.
(Continued)

*Primary Examiner* — Ann Schillinger
(74) *Attorney, Agent, or Firm* — Ping Wing; Morris, Manning & Martin, LLP

(57) ABSTRACT

A bioabsorable stent is disclosed. The stent is made of a polymer and/or non-polymer material and has an elongated body having a proximate end, a distal end, and at least one open channel formed on the exterior surface of the elongated body to provide fluid communication between the proximal end and the distal end. Also disclosed is a bioabsorable stent having an elongated center rod having a proximate end and a distal end and a plurality of leaflets extending outward from the center rod and forming channels between two neighboring leaflets to provide fluid communication between the proximal end and the distal end.

10 Claims, 28 Drawing Sheets

Related U.S. Application Data continuation-in-part of application No. 12/417,122, filed on Apr. 2, 2009, now Pat. No. 8,246,691.

(51) Int. Cl.
  *A61B 17/72* (2006.01)
  *A61F 2/82* (2013.01)
  *A61F 2/06* (2013.01)
  *A61F 2/30* (2006.01)

(52) U.S. Cl.
  CPC ... *A61F 2002/041* (2013.01); *A61F 2002/048* (2013.01); *A61F 2002/068* (2013.01); *A61F 2002/30289* (2013.01); *A61F 2230/0091* (2013.01)

(56) References Cited

U.S. PATENT DOCUMENTS

| | | | |
|---|---|---|---|
| 5,486,191 A * | 1/1996 | Pasricha | A61F 2/94 128/897 |
| 5,520,664 A | 5/1996 | Bricault, Jr. et al. | |
| 5,522,881 A | 6/1996 | Lentz | |
| 5,599,291 A * | 2/1997 | Balbierz | A61L 27/34 604/264 |
| 5,653,745 A | 8/1997 | Trescony et al. | |
| 5,827,321 A * | 10/1998 | Roubin | A61F 2/91 606/195 |
| 5,843,172 A * | 12/1998 | Yan | A61F 2/82 604/104 |
| 6,214,037 B1 | 4/2001 | Mitchell et al. | |
| 6,752,829 B2 | 6/2004 | Kocur et al. | |
| 7,131,992 B2 | 11/2006 | Iwasaka et al. | |
| 7,214,229 B2 | 5/2007 | Mitchell et al. | |
| 7,338,530 B2 | 3/2008 | Carter et al. | |
| 7,875,069 B2 | 1/2011 | Heaney et al. | |
| 7,988,716 B2 | 8/2011 | Schwartz | |
| 2003/0018306 A1 * | 1/2003 | Bucay-Couto | A61L 27/34 604/265 |
| 2003/0040754 A1 * | 2/2003 | Mitchell | A61F 2/07 606/106 |
| 2005/0038501 A1 * | 2/2005 | Moore, Jr. | A61F 2/91 623/1.19 |
| 2005/0080478 A1 | 4/2005 | Barongan | |
| 2005/0085891 A1 | 4/2005 | Goto et al. | |
| 2005/0090888 A1 | 4/2005 | Hines et al. | |
| 2005/0119730 A1 | 6/2005 | Howat et al. | |
| 2006/0100689 A1 | 5/2006 | Pryor | |
| 2006/0265054 A1 | 11/2006 | Greenhalgh et al. | |
| 2007/0032880 A1 * | 2/2007 | Maeda | A61M 27/008 623/23.7 |
| 2007/0129787 A1 | 6/2007 | Bezwada | |
| 2007/0270939 A1 | 11/2007 | Hood et al. | |
| 2007/0293963 A1 | 12/2007 | Jung et al. | |
| 2008/0140176 A1 | 6/2008 | Krause et al. | |
| 2008/0200976 A1 | 8/2008 | Asgari | |
| 2008/0319536 A1 | 12/2008 | Houston et al. | |
| 2009/0024204 A1 | 1/2009 | Greenhalgh et al. | |
| 2009/0187240 A1 | 7/2009 | Clerc et al. | |
| 2009/0204082 A1 | 8/2009 | Wesselmann et al. | |
| 2010/0256729 A1 | 10/2010 | Mangiardi | |
| 2011/0004320 A1 * | 1/2011 | Priplata | A61F 2/04 623/23.65 |

OTHER PUBLICATIONS

Notification of Transmittal of the International Search Report and the Written Opinion of the International Searching Authority, or the Declaration, Korean Intellectual Property Office, Form PCT/ISA/220 of International Application No. PCT/US2009/069786.

Yuan, X., et al., "Characterization of Poly(L-lactic acid) Fibers Produced by Melt Spinning", Journal of Applied Polymer Science, vol. 81, pp. 251-260 (2001).

Carlson, R.P., et al., "Anti-biofilm Properties of Chitosan-coated Surfaces", J. Biomater. Sci. Polymer Edn., vol. 19, No. 8, pp. 1035-1046 (2008).

Van De Velde, K., et al. "Biopolymers: Overview of Several Properties and Consequences on Their Applications", Polymer Testing, vol. 21, pp. 433-442 (2002).

Donelli, G., et al., "Plastic Biliary Stent Occlusion: Factors Involved and Possible Preventive Approaches", Clin Med Res., vol. 5, No. 1, pp. 53-60 (2007).

Somogyi, L., et al. "Biliary and Pancreatic Stent", Gastrointestinal Endoscopy, vol. 63, No. 7, pp. 910-919 (2006).

File History of U.S. Appl. No. 12/539,314, filed Aug. 11, 2009.

\* cited by examiner

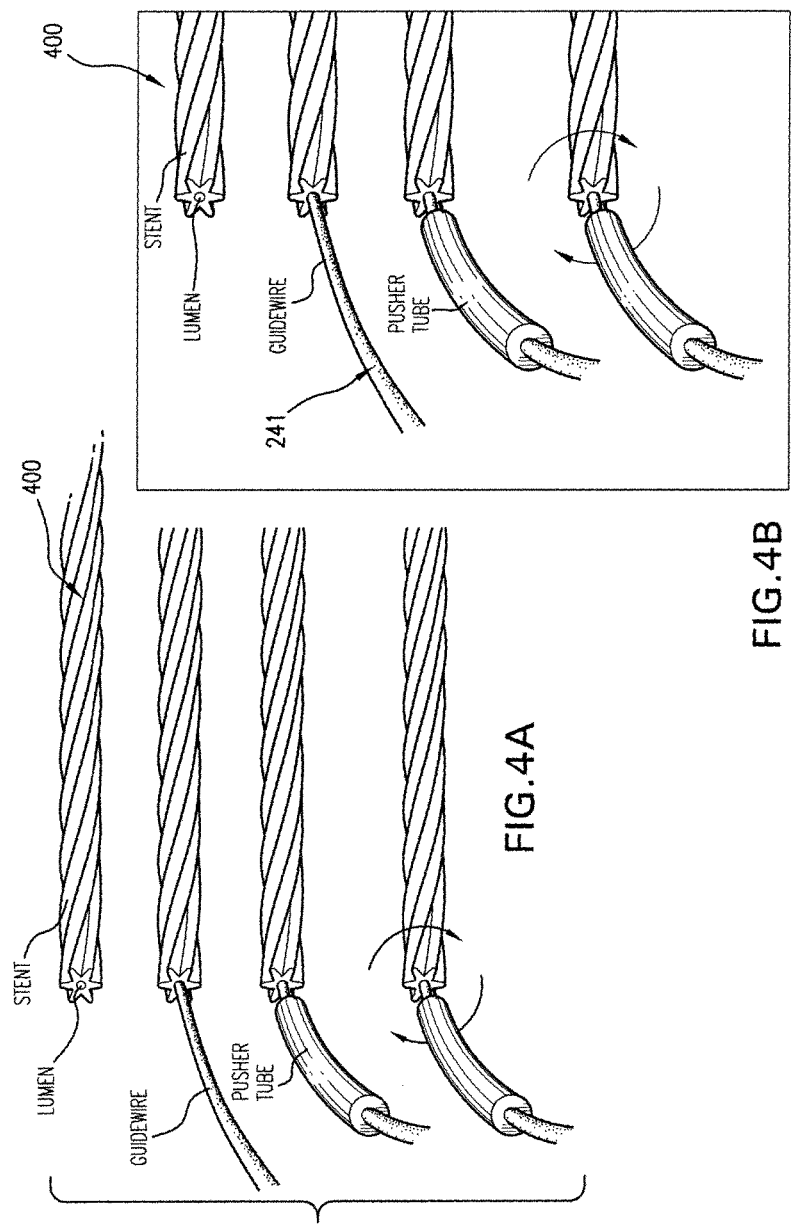

STENT

This application is a Continuation of U.S. application Ser. No. 12/539,314, filed Aug. 11, 2009, which is a Continuation-In-Part of U.S. application Ser. No. 12/417,122, filed on Apr. 2, 2009, now U.S. Pat. No. 8,246,691. The entirety of the aforementioned applications is incorporated herein by reference.

FIELD

The present invention generally relates to medical devices and, in particular, to a stent with one or more open channels formed on its exterior surface.

BACKGROUND

In medical terms, a stent is a man-made "tube" inserted into a natural passage or conduit in the body to prevent, or counteract, a disease-induced, localized flow constriction. The term may also refer to a tube used to temporarily hold such a natural conduit open to allow access for surgery. Stents include vascular and non-vascular stents. Vascular stents are designed for applications in the vascular system, such as arteries and veins. Non-vascular stents are used in other body lumens such as biliary, colorectal, esophageal, ureteral and urethral tract, and upper airway Stents are available in permanent and temporary varieties. Stent duration is heavily influenced by the construction material. For example, metal stents typically have a much longer use life than plastic stents. The stent body typically has a central lumen that allows blood or other body fluid to flow through the stent. A common problem with the current stents is that they routinely migrate and clog, thus requiring additional procedures for extraction and/or replacement. There exists a need for improved stents that are easy to make and safe to use.

SUMMARY

A bioabsorable stent is disclosed. The stent includes an elongated stent body having a proximate end, a distal end, and at least one open channel formed on the exterior surface of the elongated stent body to provide fluid communication between the proximal end and the distal end.

In one embodiment, the elongated body comprises a polymer material.

In a related embodiment, the polymer material comprises bioabsorable polymers, transparent plastic polymers, thermoplastic polyurethane or silicone polymers.

In one embodiment, the elongated body comprises a non-polymer material.

In a related embodiment, the non-polymer material comprises stainless steel, cobalt alloys such as cobalt-chromium, titanium alloys, tantalum, niobium, tungsten, molybdenum or nitinol. In a related embodiment, the open channel is a sinusoidal channel on the exterior surface of the elongated stent body.

In another embodiment, the elongated body comprises a combination of a polymer and a non-polymer material.

In another related embodiment, the elongated stent body is made of a magnesium and chitin alloy.

In another related embodiment, the elongated stent body is made with a magnesium core coated with a chitin chitosan, N-acylchitosan hydrogel outer layer. The magnesium core may additionally include rare earth materials.

In another related embodiment, the elongated stent body is made of a chitin and chitosan, N-acylchitosan hydrogel and magnesium alloy with raw earth elements.

In another related embodiment, the sinusoidal channel has a concentrically consistent pitch.

In another related embodiment, the sinusoidal channel has a concentric pitch that changes in its length over the device.

In a related embodiment, the open channel extends from the proximal end to the distal end of elongated stent body in a zig-zag form.

In another related embodiment, the elongated stent body comprises a plurality of channels on the exterior surface.

In another related embodiment, the distal end and the proximate end of the channels have different diameters.

In another related embodiment, the distal end and the proximate end of the stent have different diameters.

In another related embodiment, the open channel has different depths from one end of the stent to the other or intermittently at varying points through the length of the stent.

In another embodiment the open channel has varying diameters.

In another embodiment, the ends of the elongate stent body have different shapes.

In another related embodiment, the elongated stent body has a sinusoidal shape.

In another related embodiment, the elongated stent body further includes a center lumen.

In another related embodiment, the sinusoidal pitch may span or extend over the entire length of an interior surface of the stent body.

In another related embodiment, the sinusoidal pitch may span or extend over a portion of an interior surface of the stent body or only a portion of an exterior surface of the stent body.

In another related embodiment, the sinusoidal pitch may span or extend over the interior surface and exterior surface of the device throughout its wall thickness or over a portion of its wall thickness or over a portion of the interior surface and exterior surface of the stent body.

In another related embodiment, the elongated stent body further includes an anchoring device.

In another related embodiment, the elongated stent body further includes a biological agent.

In another related embodiment, the biological agent is selected from the group consisting of chemotherapeutic agents, antimicrobial agents and gene transfer agents.

In another related embodiment, the open channel is formed by compressible channel walls that can be compressed against each other in a compressed state to reduce the diameter of the stent.

Also disclosed is a stent having an elongated stent body with a proximate end, a distal end, and at least one sinusoidal channel or track on an exterior surface of the body to provide fluid communication between the proximal end and the distal end. The distal end and the proximate end of the stent have different diameters.

In a related embodiment, the elongated stent body is made of a non-polymer material.

In another related embodiment, the elongated stent body further contains a center lumen.

In another related embodiment, the sinusoidal channel is formed between two collapsible channel walls.

Also disclosed is a stent that includes an elongated center rod having a proximate end and a distal end, and a plurality of leaflets extending outward from the center rod and forming channels between two neighboring leaflets to provide fluid communication between said proximal end and said distal end. The center rod and the leaflets are made of a bioabsorable material.

In a related embodiment, the plurality of leaflets can be folded to reduce the diameter of the stent.

In a related embodiment, the plurality of leaflets can be folded pivotally over each other.

Also disclosed is a kit for stent implantation. The kit includes: a stent having an elongated stent body with a proximate end, a distal end, and at least one open channel formed the exterior surface of the body to provide fluid communication between the proximal end and the distal end; a guide wire; and a pusher tube that is movable along the guide wire.

In a related embodiment, the elongated stent body is made of a non-polymer material.

In another related embodiment, the elongated stent body of the stent further contains a center lumen to adopt the guide wire.

In another related embodiment, the elongated stent body is made of a mixture of compounds.

In another related embodiment the elongated stent body is made of a magnesium and chitin alloy.

In another related embodiment, the elongated stent body is made with a magnesium core coated with a chitin chitosan, N-acylchitosan hydrogel outer layer. The magnesium core may additionally include rare earth materials.

In another related embodiment, the elongated stent body is made of a chitin and chitosan, N-acylchitosan hydrogel and magnesium alloy with raw earth elements.

Also disclosed is a method for stabilizing bone fracture. The method includes inserting the stent of the present invention into the canal of a bone having a fracture.

In a related embodiment, the stent is coated with a hydrogel. The hydrogel expands by absorbing of fluids and improves the connection and support of the inner wall of the bone canal.

In another related embodiment, the stent is used to attach bone fractures together.

In another embodiment, the stent is placed through the bone cortex.

In another embodiment, the stent is imbedded with barium sulphate or other metallic particles or contrast agents to allow all or a part of the stent to be seen under imaging.

In another embodiment, the stent is coated with a biodegradable material to control its properties, including mechanical strength, biocompatibility, biodegradation, diffusibility, and absorption properties.

In another embodiment, the stent degrade in situ by hydrolytic reactions, enzymatic reactions, alkaline or pH elevations.

BRIEF DESCRIPTION OF THE DRAWINGS

The present invention can be better understood by reference to the following drawings, wherein like references numerals represent like elements. The drawings are merely exemplary to illustrate certain features that may be used singularly or in combination with other features and the present invention should not be limited to the embodiments shown.

FIGS. 4A and 4B are diagrams showing two engagement mechanisms among the stent, the guide wire and the pusher tube.

DETAILED DESCRIPTION

Figure 1A:
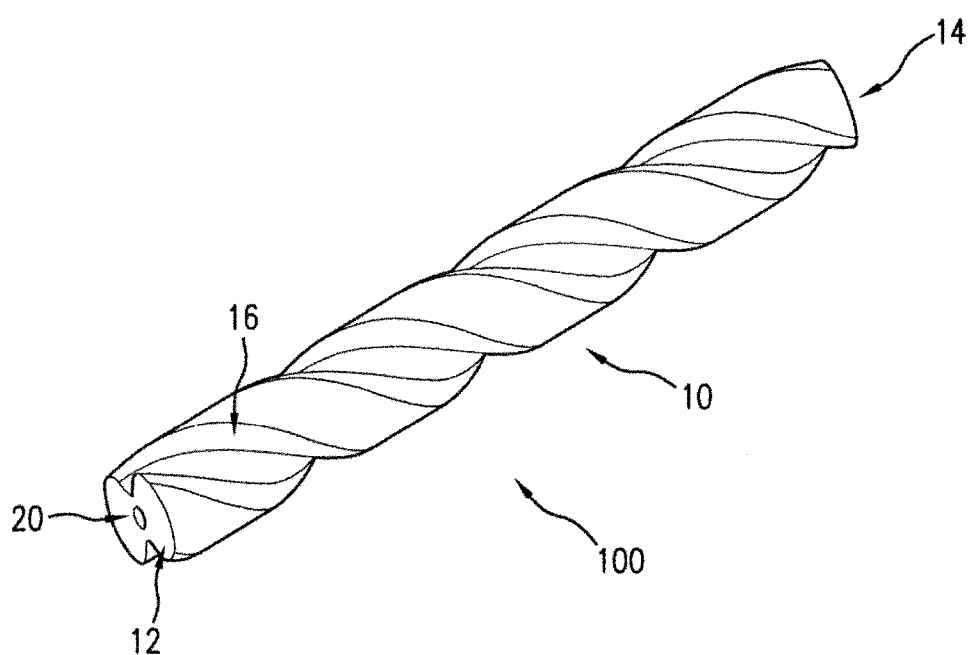
FIG. 1A is a diagram showing an embodiment of the stent of the present invention.

The practice of the present invention will employ, unless otherwise indicated, conventional medical devices and methods within the skill of the art. Such techniques are explained fully in the literature. All publications, patents and patent applications cited herein, whether supra or infra, are hereby incorporated by reference in their entirety.

One aspect of the present invention relates to a stent that contains an elongated stent body having a proximate end, a distal end, and at least one open channel formed on the exterior surface of the elongated stent body to provide fluid communication from the proximal end to the distal end of the stent.

As used herein, the term "stent" refers to a device which is implanted within a bodily lumen to hold open the lumen or to reinforce a small segment of the lumen. Stents can be used for treating obstructed vessels, biliary ducts, pancreatic ducts, ureters, or other obstructed lumens, fractured canals, bones with hollow centers and/or for delivering various drugs through controlled release to the particular lumen of interest.

The open channel should be large enough to allow unobstructed or normal flow of various body fluids such as blood, bile or urine or other luminal material/liquids on the outer aspect of the stent. The open channel may have a cross section area that is of any shape or depth. The channel could be V shapes, U shaped, or with a rising or falling pitch, of an even depth or one that is of varying widths, depths, varying and circumferential rotations changing at various points over the length of the device. The channel can be a straight channel or a spiral channel. Multiple channels may be formed on the exterior surface or the inner surface of the elongated stent body. The channel(s) may also be designed with a geometry that would help the stent to remain in place.

The shape, length and diameter of the stent body are application dependent. The elongated stent body can be straight or curved or in the shape of multiply connected and angulated curves. Each type of stent is designed to fit within a specific part of the anatomy. Therefore, the shape, length, and diameter of stents differ by type to accommodate and support different sized lumens and different clinical needs. For example, each major stent application, such as vascular, pancreatic, ureteral, or metacarpal canal, other hollow bone structures and other stent, requires a different diameter and shape to enable placement, to remain in place after placement, to stabilize and support the anatomy it is placed in, and to allow conformance to the normal anatomy. As used herein, the diameter of a stent refers to the width across the shaft of the stent body, which is also referred to as the "major diameter." In one embodiment, the stent has a uniform diameter. In another embodiment, the stent has a variable diameter. In one embodiment, the diameter at the distal end is smaller than the diameter at the proximate end. In another embodiment, the diameter at the proximate end is smaller than the diameter at the distal end. In yet another embodiment, the diameters at the distal end and the proximate end are both smaller than the diameter at the middle section of the stent.

The stent body may further include a center lumen to accommodate a guide wire. This center lumen may provide additionally flow throughput after the removal of guide wire.

In one embodiment, the stent is naturally formed by braiding multiple filaments together. In another embodiment, the stent is made with a center rod/hub/cam having one or more sinusoidal channels running through the exterior surface of the center rod, similar to that of a drillbit.

The stent of the present invention can be expandable. In one embodiment, the stent is of two different diametrical dimensions due to radial deformation of its elastic elements. Before being positioned at the place of reconstruction, the stent is deformed/compressed/folded so as to minimize its diametrical dimension. Then the stent is placed, in the deformed state, inside a transporting means by arranging it on a special setting bulb. Once the stent has been transported to the place of reconstruction, the setting bulb is expanded so that the stent diameter is maximized. In another embodiment, the stent has a plurality of flexible or foldable channel walls or leaflets extending from the center rod/hub/cam. The channel walls or leaflets are kept in a folded position during the delivery process and are released only at the treatment site.

In one embodiment, the stent is delivered to the treatment site in a body lumen with a pusher rod that pushes the stent through a body channel into place. The pusher rod travels over a guide wire. The pusher rod is designed in such a way to attach to the ends of the stent to assist with directing the delivery. In one embodiment, the pusher rod interlocks with the proximate end of the stent in a male/female fashion, much the same way a wrench fits over a nut.

Figure 1B:
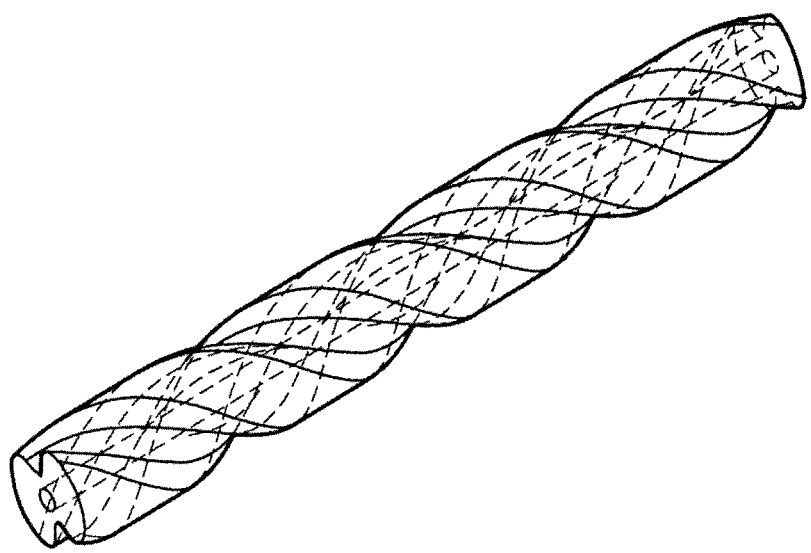
FIG. 1B is a see-through illustration of FIG. 1A.

FIG. 1A is a diagram showing an embodiment of the stent of the present invention. In this embodiment, stent 100 has an elongated body 10 with a proximate end 12 and a distal end 14. Two sinusoidal channels 16 are formed on the exterior surface of the elongated body 10, extending from the proximate end 12 to the distal end 14 in a fashion similar to the grooves on a drill head. The channels may have beveled edges to facilitate fluid flow inside the channels. The channels can be of varying depths and lengths. The ends of the stent body can be of various shapes including conical shape. FIG. 1B is a see through drawing of FIG. 1A. The two-channel design allows for two channels on the exterior surface of the stent to run in parallel from one end to the other or to criss-cross to allow for increased fluid flow as well as the ability to increase side branch flow of the main stented channel.

A center lumen 20 allows the stent 100 to slide into the place of implantation through a guide wire.

Figure 2:
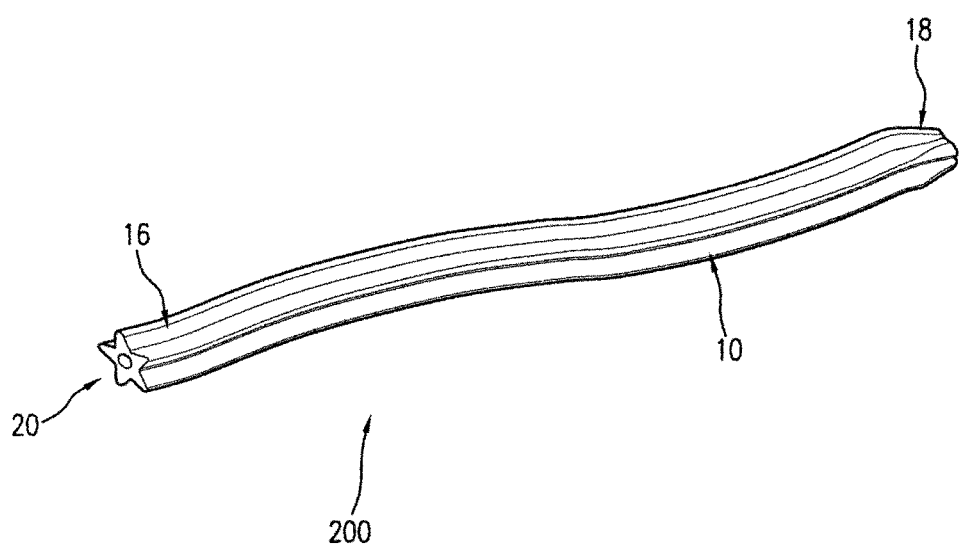
FIG. 2 is a diagram showing a stent with a sinusoidal shaped stent body.

FIG. 2 shows another embodiment of the stent of the present invention. In this embodiment, stent 200 has a modified sinusoidial body shape to improve flexibility, allow for varying flow dynamics, and facilitate contour and wall adherence to the lumens. The multiple V shaped channels 16 allow for the flow of various body fluids. The diameter of the internal lumen 20 and the outer diameter of the stent body can be changed based on the need for various luminal dimensions, shapes, flows, and biomechanics. The tapered tip 18 facilitates advancement of the stent inside a body lumen.

Figure 13:
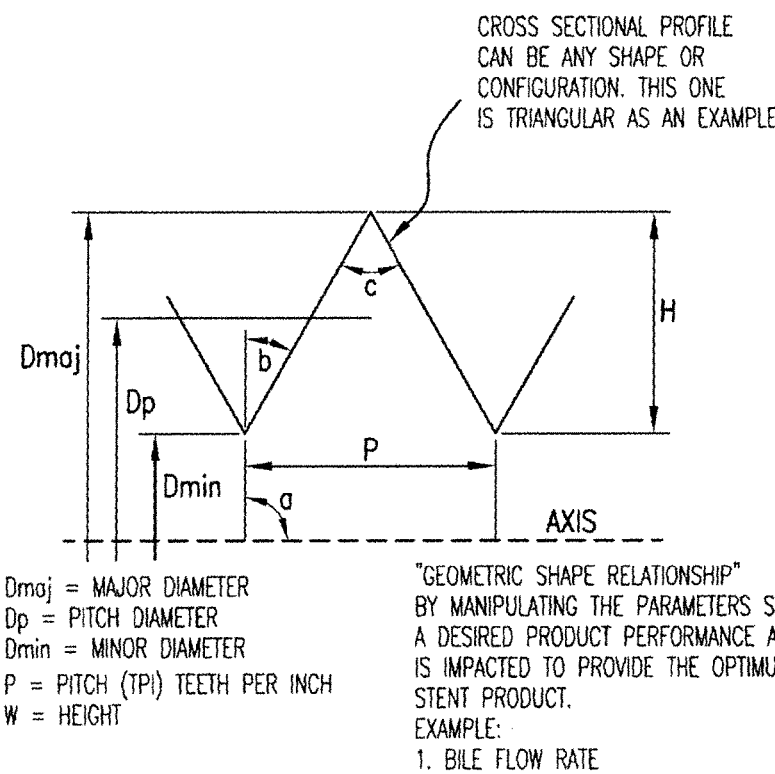
FIG. 13 shows the cross section of an embodiment of a stent of the present invention.
Figure 14:
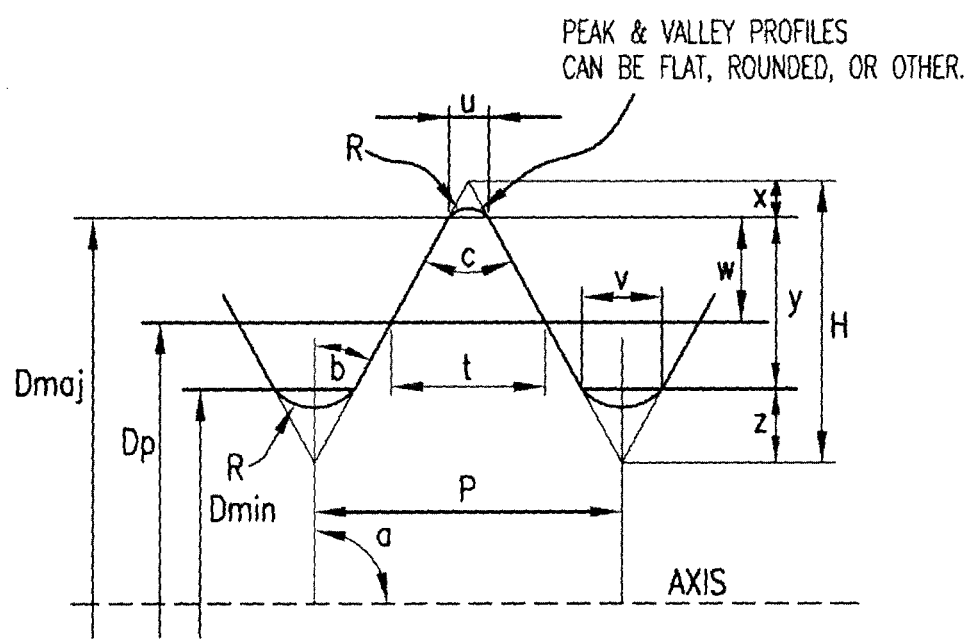
FIG. 14 shows the cross section of another embodiment of a stent of the present invention.

FIGS. 13 and 14 show cross-sections of V-shaped channel and channel walls. The channels can be of varying depths and varying widths to change the volume and speed of fluid flow. The bottom of the channel can be rounded or tapered or formed by a direct angle.

Figure 3:
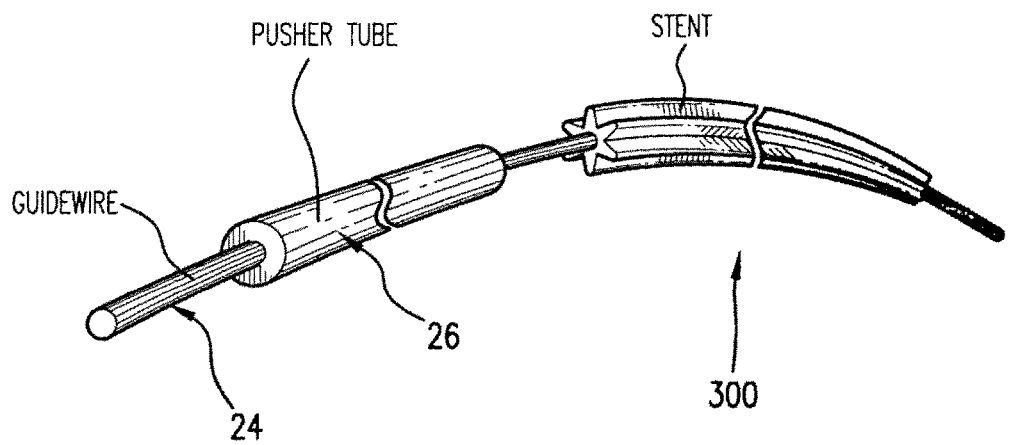
FIG. 3 is a diagram showing an assembly of a stent with a guide wire and a pusher tube.

The stent of the present invention may be implanted with procedures well known to a person of ordinary skill in the art. Examples of such procedures include, but are not limited to, standard percutaneous approach using a guide wire, endoscopic retrograde cholangiopancreatography (ERCP) placement procedures, and other radiographic/angiographic procedures. FIG. 3 shows an assembly of a stent 200 with a guide wire 24 and a pusher tube 26. FIG. 4 shows several engagement mechanisms among the stent 300, the guide wire 24 and the pusher 26. In FIG. 4A, the pusher tube has several fingers to hold the stent 300 like a hand or clamp. In FIG. 4B, the pusher 26 interlocks with the stent 300 in a male/female fashion to ensure security of positioning and delivery of the stent 300. The interlacking mechanism may involve a male to female interconnect of various shapes, sizes, or dimensions.

Figure 5A:
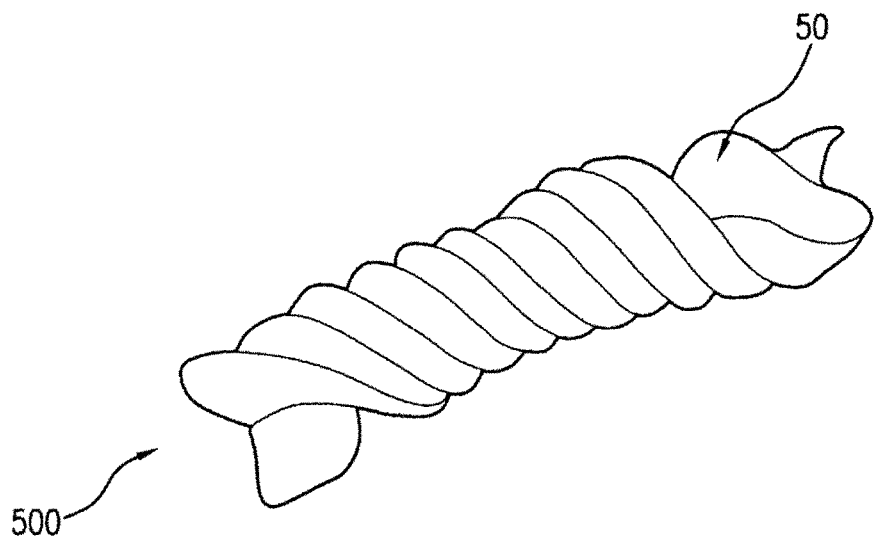
FIGS. 5A and 5B show an embodiment of an expandable stent.
Figure 5B:
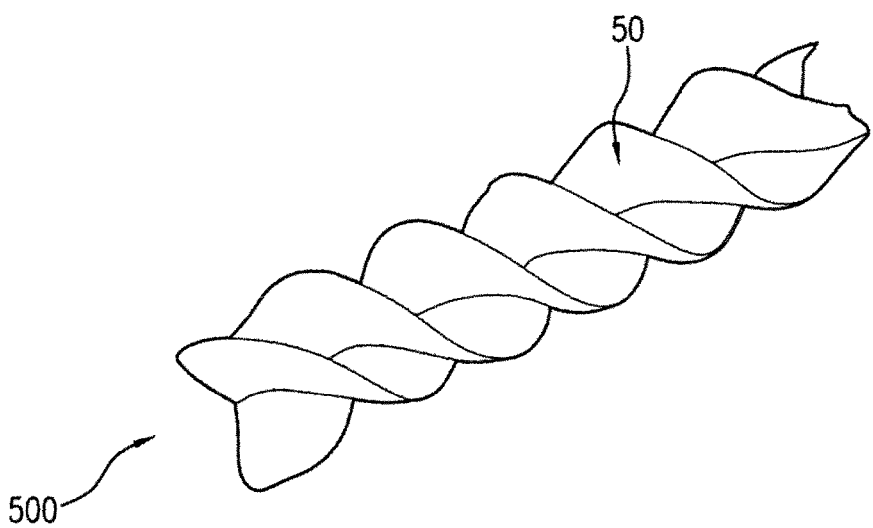

FIGS. 5A and 5B show an embodiment of an expandable stent 500 with compressible channel walls 50. In a closed state (FIG. 5A), the channel walls 50 are compressed or twisted against each other to reduce stent diameter. Once the stent has been transported to the treatment site, the channel walls are restored to their natural shape (FIG. 5B).

Figure 6A:
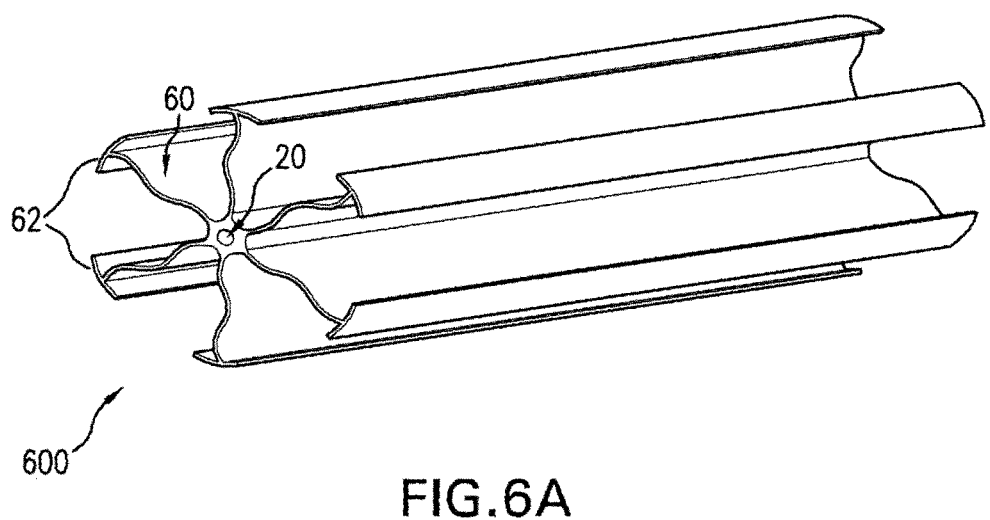
FIGS. 6A and 6B show another embodiment of an expandable stent.
Figure 6B:
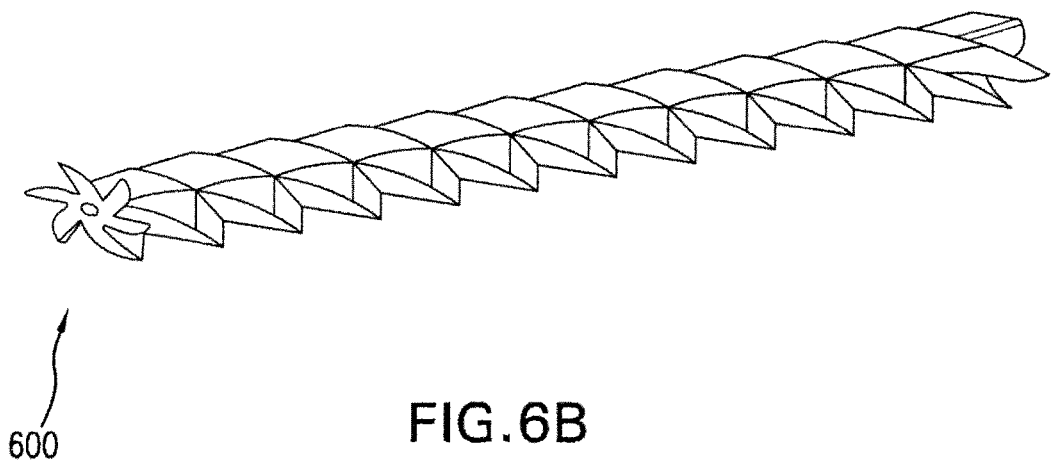

FIGS. 6A and 6B show another embodiment of an expandable stent 600 with foldable leaflets 60. In an extended state, the thin leaflets 60 allow for unobstructed flow of body fluid (FIG. 6A). In one embodiment, the leaflets 60 are contoured and aligned in a way to increase the flow speed of the body fluid or to provide minimal drag. The impedance of the flow volumes and the velocity can be modulated by changing the angles and contour of the leaflets. Additionally the interconnecting supports can be thicker at the cam to provide different levels of stability and rigidity for the bracing arms 62, which help support the structure they are placed in. The bracing arms 62 can be connected at anywhere along their diameter and the change in connection points will have an impact I the rigidity of the support of the lumen, the ability of the device to flex with the normal body movement of the lumen and will change the minimal diameter the device can be collapsed in. The stent 600 may further contain a center lumen 20.

As shown in FIG. 6B, the leaflets 60 may be rotated pivotally (e.g., clockwise) to collapse into each other to reduce the size of the stent to facilitate implantation. Once in place, the stent may be rotated in an opposite direction (e.g., counter clockwise) to restore to its extended state. The tip of the stent 600 can be titled or coned or shaped into various configurations to allow for access to different body lumens. The opened leaflets 60 further have the benefit to prevent migration of the stent 600.

Figure 7A:
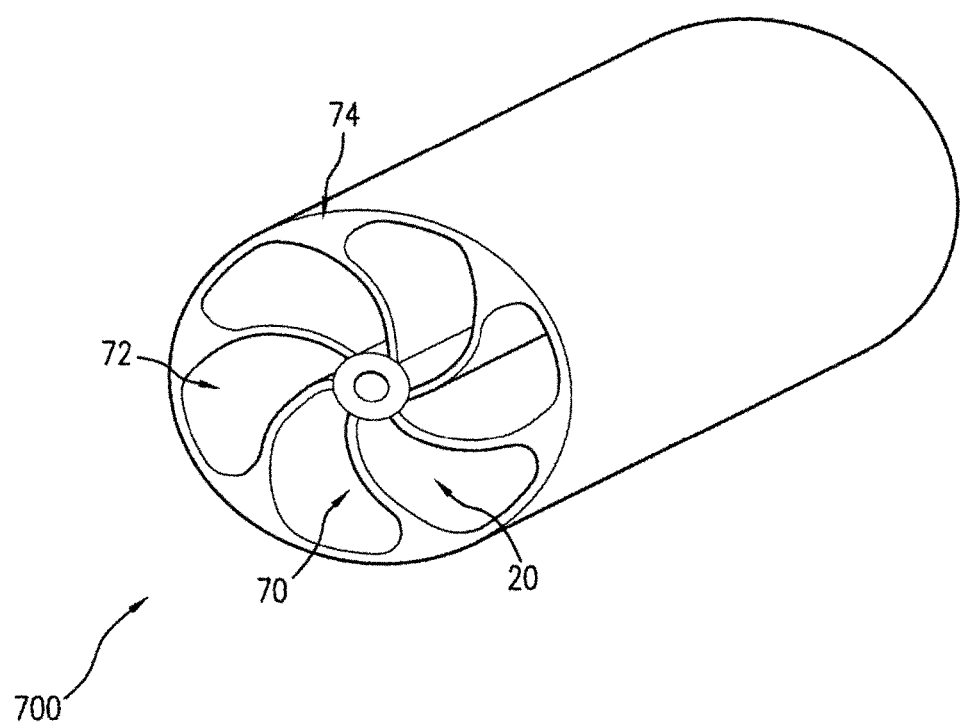
FIGS. 7A and 7B show another embodiment of an expandable stent.
Figure 7B:
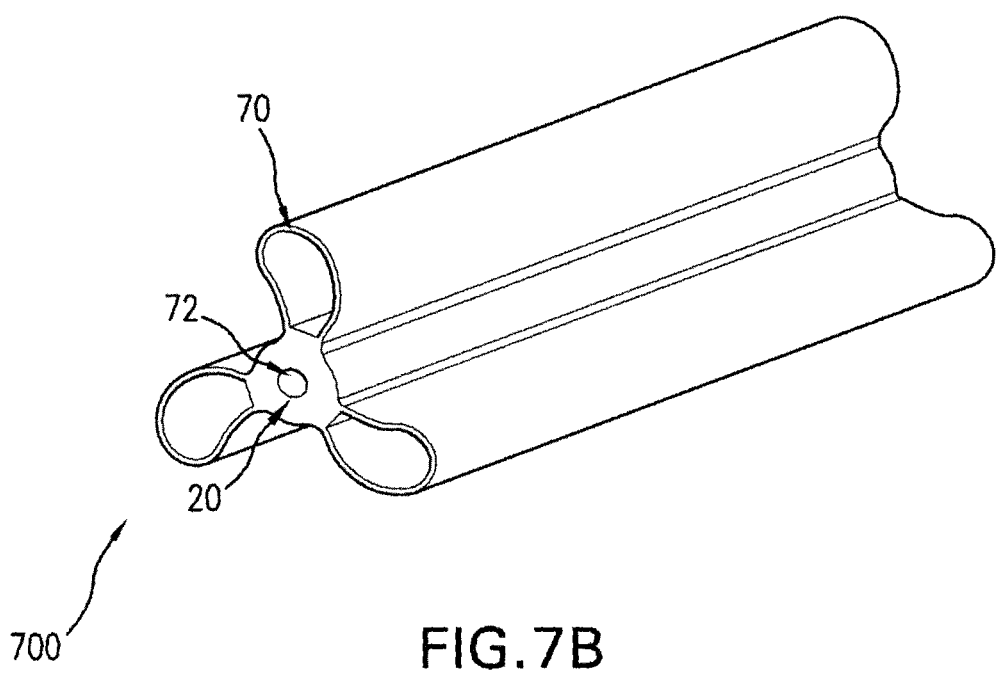

FIGS. 7A and 7B show another embodiment. In this embodiment, the expandable stent 700 has closed connections around each alternating leaflet 70 to allow for changes in flexibility, radial force, compression resistance, and absorption. The leaflets 70 have a sinusoidal pattern and can be thicker at the attachment to inner cam 72 to allow for variations of rigidity. The outer cam 74 prevents tissue growth inside the stent body and increases contact area between the stent 700 and inner wall of the body lumen. The thickness of outer cam 74 is application dependent. The outer cam 74 may also be beveled. The stent 700 may have a removal grip attached to the end of center lumen 20 to allow for easy removal of the stent 700.

FIG. 7B shows another embodiment of the stent 700. In this embodiment, the leaflets 70 are connected to the cam 72 and can be compress down towards the cam 74. The leaflets may have a hollow interior so that fluid may flow through and around the leaflets 70.

Figure 8A:
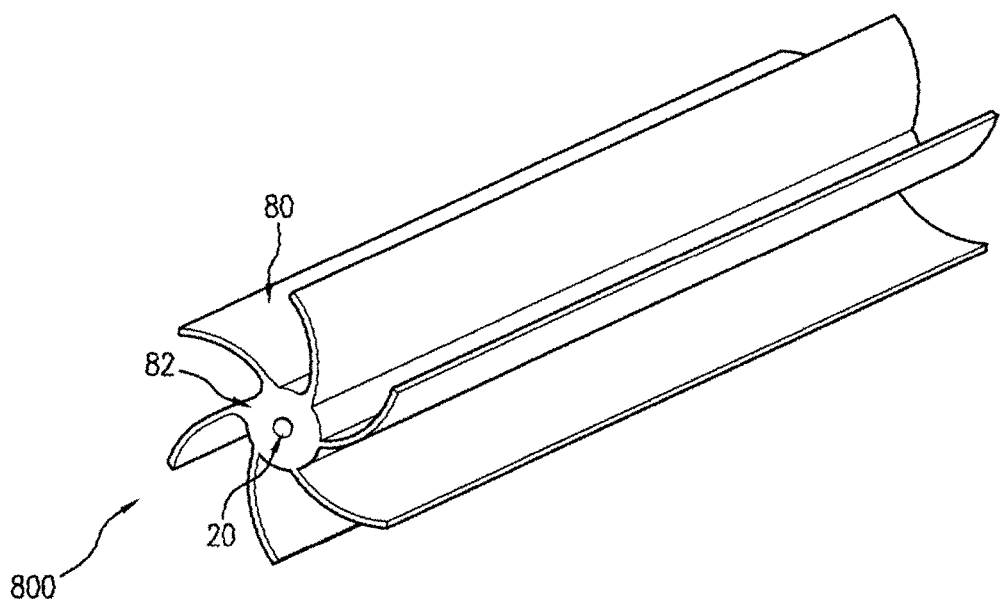
FIGS. 8A-8F show various embodiments of an expandable stent.

In another embodiment, stent 800 contains propeller-like leaflets 80 that are thicker at the base where they are attached to the cam or rod portion 82 of the stent 800. The leaflets 80 become thinner at the tip (FIG. 8A). The stent 800 may also have a sinusoidal shape to conform to a body lumen.

Figure 8B:
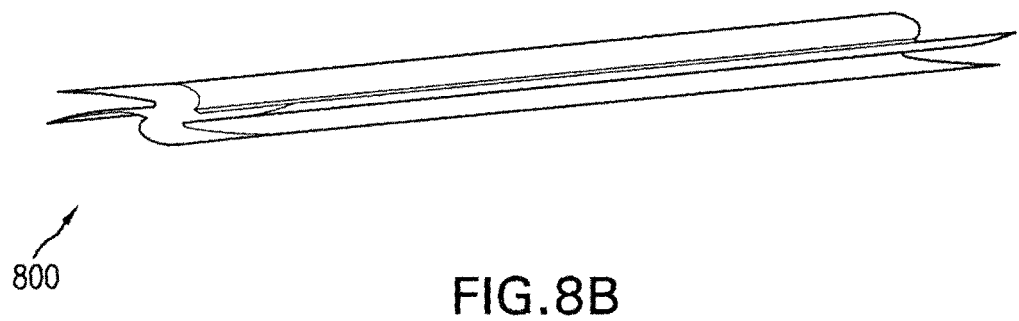

The propeller-like stent 800 may be constructed in such a way to allow unidirectional collapse of the leaflets to facilitate ease of passage through the working channel of an endoscope, bronchoscope, or through some other tubular delivery apparatus or opening by simply rotating the stent in a unidirectional manner and then reversing the technique to open the stent once it is in place. Additionally, the tip of the stent 800 may be shaped to allow for ease of collapse or insertion. FIG. 8B shows a stent 800 in a collapsed configuration.

Figure 8C:
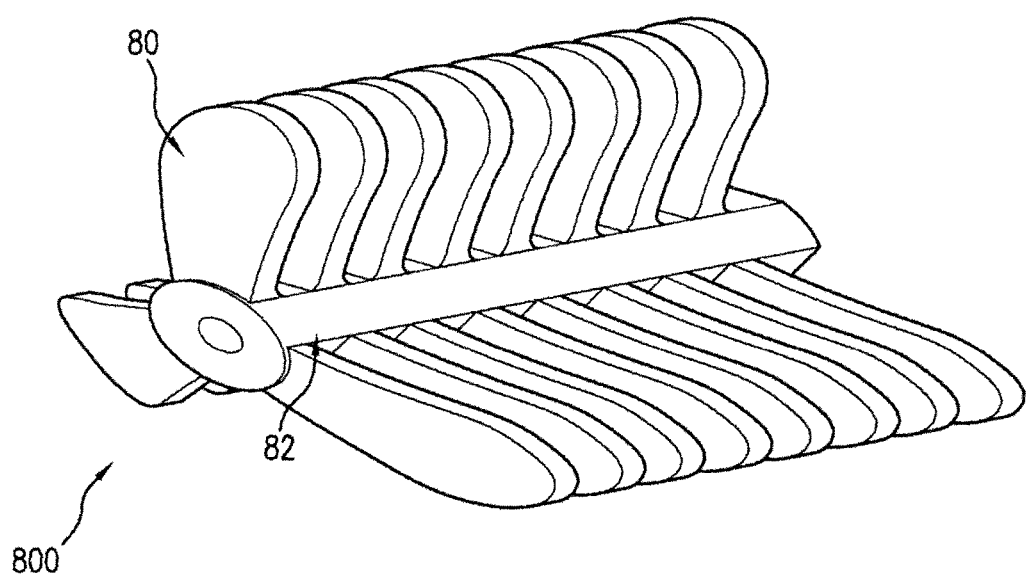
Figure 8D:
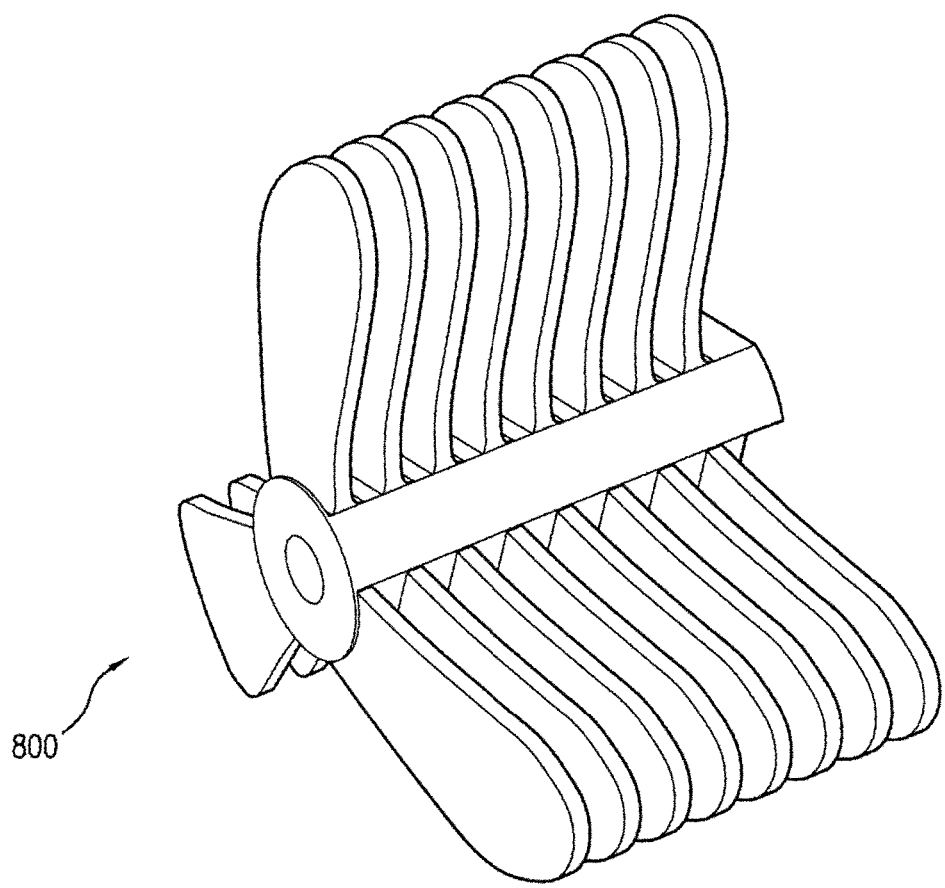

FIG. 8C shows another embodiment of the stent 800. In this embodiment, the leaflets 80 can be folded towards the cam or rod portion 82 of the stent body, in a manner similar to that of an umbrella. The leaflets 80 can be in any shape, such as round, oval, triangle etc. and will have a change in thickness at the base where the leaflets are connected to the cam 82 to allow you to change ease or rigidity of folding the device and passing it through and opening or channel. The unidirectional leaflets allow the device to be pushed through an opening and then pulled back to secure it in place. In another embodiment, the leaflets can be folded towards the cam or rod portion of the stent body, in a manner similar to that of an umbrella, a collapsing tree, or unidirectional or multidirectional folding leaflets of consistent or varying shapes. FIG. 8D shows the stent of FIG. 8C in a collapsed configuration.

Figure 8E:
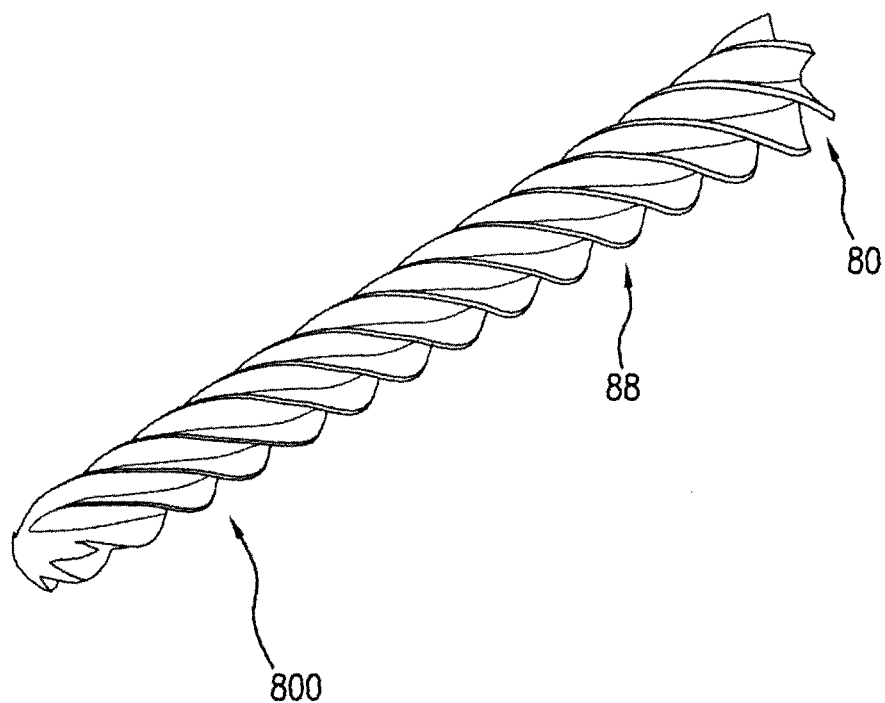
Figure 8F:
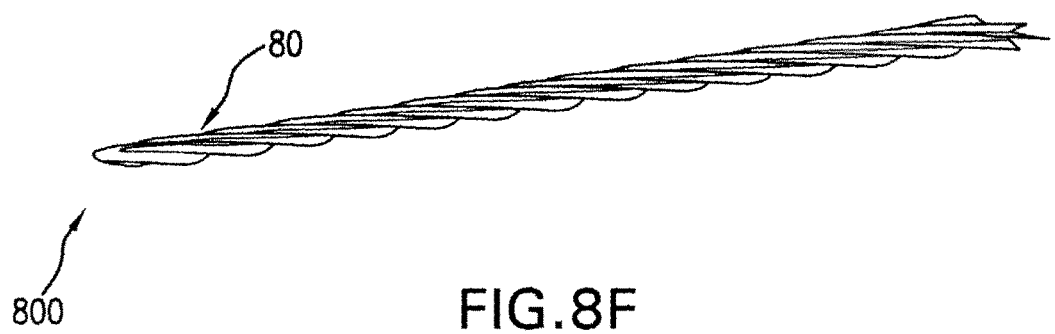

In another embodiment, the leaflets 80 of the stent 800 can be folded together by rotating along a common axis. FIGS. 8E and 8F show a stent 800 in open and folded configurations, respectively. In one embodiment, the stent 800 has a diameter of 1 cm in open configuration and a diameter of 1 mm in folded configuration. Depending on flow requirements, the channel 88 may have raps ranging from 5.degree. to 100.degree. In certain embodiments, the channel has a rap of 5.degree., 10.degree., 20.degree., 30.degree., 40.degree., 50.degree., 60.degree., 70.degree., 80.degree., 90.degree., or 100.degree.

In another embodiment, a device has a portion of the device and stent and its leaflets collapsible so that some portion of the device (e.g., 1%) would have uni-direction leaflets and the remainder would have the opposite facing leaflets or directions such as seen on the different blades of a saw. In yet another embodiment, the leaflets are alternating in directions so as to prevent migration of the expanded stent.

Figure 9A:
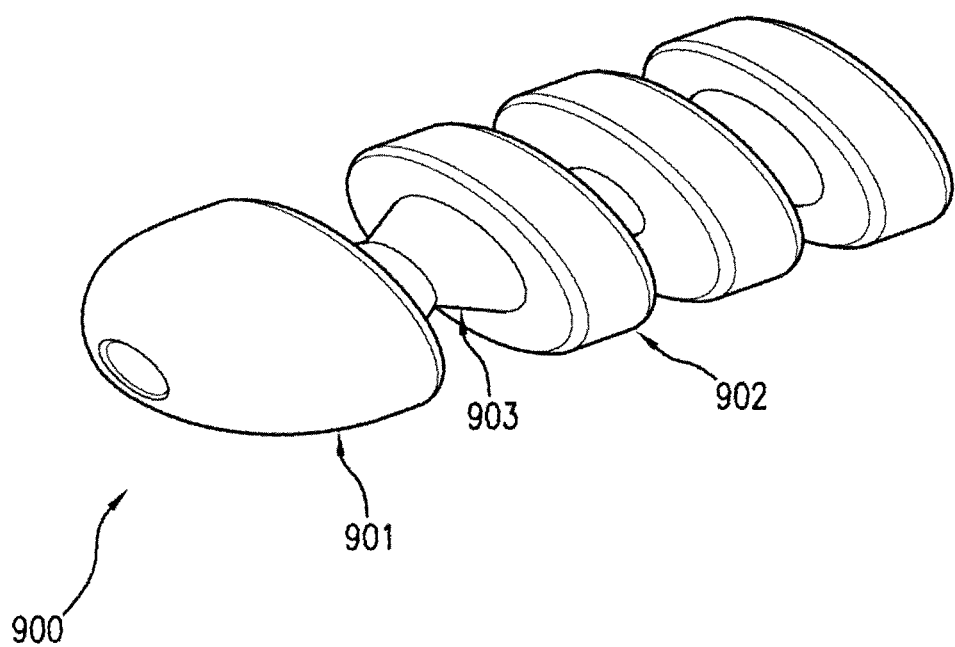
FIGS. 9A-9C show several embodiments of a stent with an outer frame.
Figure 9B:
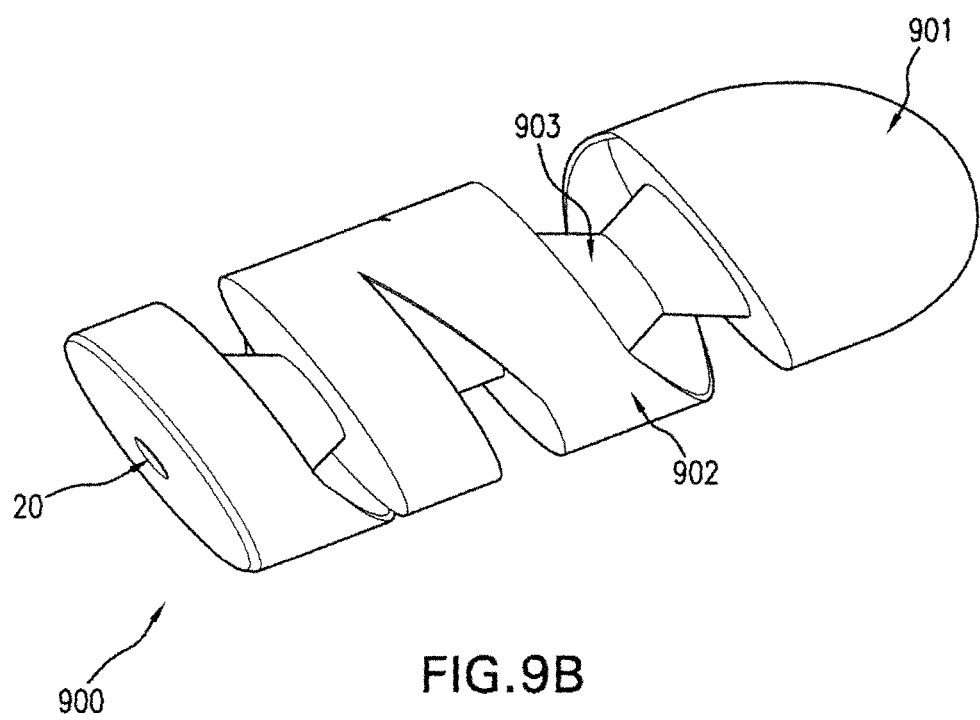
Figure 9C:
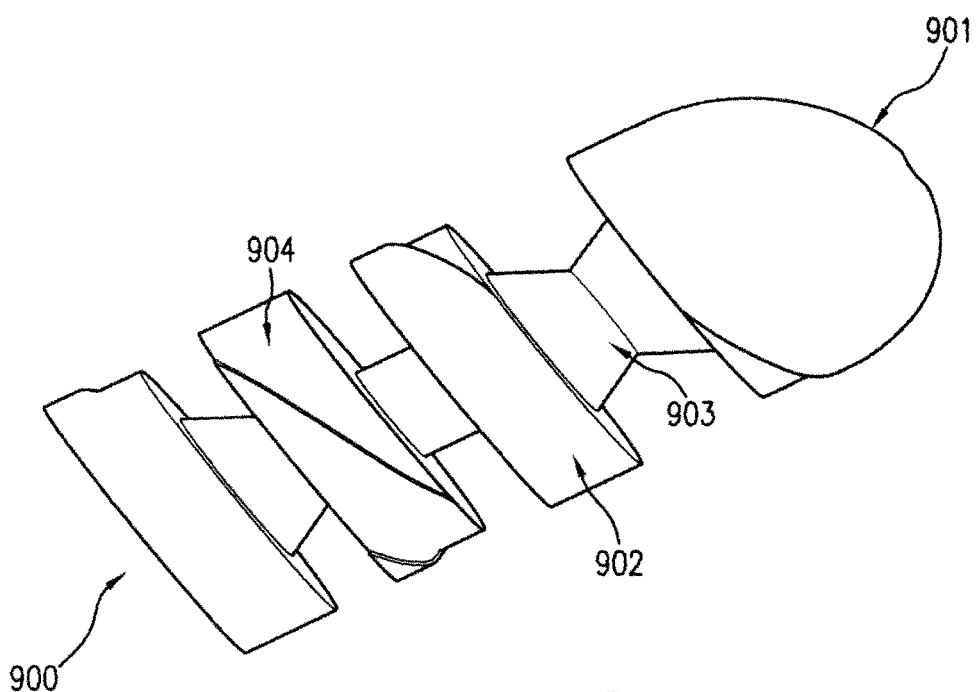

Referring now to FIG. 9A an embodiment of stent 900 has a tapered proximal end 901 to allow ease of passage inside a body lumen, an outer frame 902 with a larger diameter to provide stiffness, and a center core 903 with a smaller diameter to provide flexibility. The outer frame 902 and the center core 903 can be cylindrical or cut with various contours in the surface to change the flexibility or rigidity of the stent. In FIG. 9B, the stent 900 has an outer frame 902 that forms a coil around the core 903. The stent 900 may further include a center lumen 20. In FIG. 9C, the stent 900 has sinusoidal channel 904 formed on the surface of outer frame 902. The channel 904 may have variable depth. The center core 903 may have various shapes and sizes to adjust the flexibility, stability and rigidity of the stent 900.

In one embodiment, the stent 900 is inserted into the canal of a bone having a fracture. In another embodiment, the stent 900 is coated with a hydrogel. The hydrogel expands by absorbing of fluids and improves the connection and support of the inner wall of the bone canal. In another embodiment, the stent 900 is used to attach bone fractures together. In another embodiment, the stent 900 is placed through the bone cortex.

Figure 10:
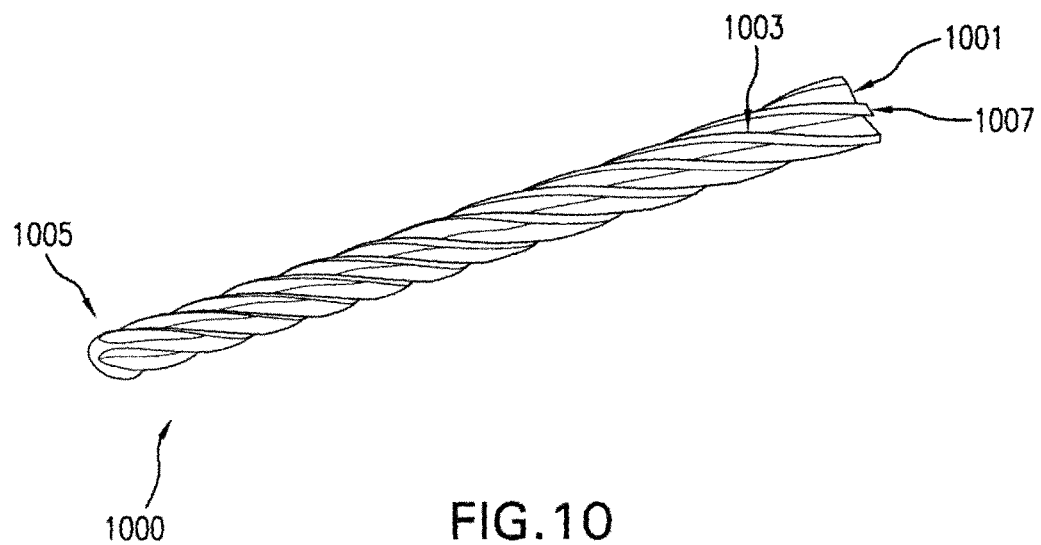
FIG. 10 shows another embodiment of a stent with sinusoidal channels of varying pitches.

Referring now to FIG. 10, another embodiment of a stent 1000 has channels of varying widths and depths on the exterior of the stent body. For example channel 1001 has a width that is greater than the width of channel 1003. The variable width and depth can be used to change the flow of fluids or friction to the lumen it is place in. Similar channels may also be formed on the interior side of a tubular stent. In the embodiment shown in FIG. 10, the stent 1000 has a tapered tip 1005 to facilitate advancement of the stent inside a body lumen. The wide distal flare 1007 prevents migration and increases stability of the stent 900. The stent 1000 may have channels of shorter or longer pitches to enable increases in fluid flow and stability. The stent 1000 may further include a center lumen for a guide wire or fluid flow.

Figure 11A:
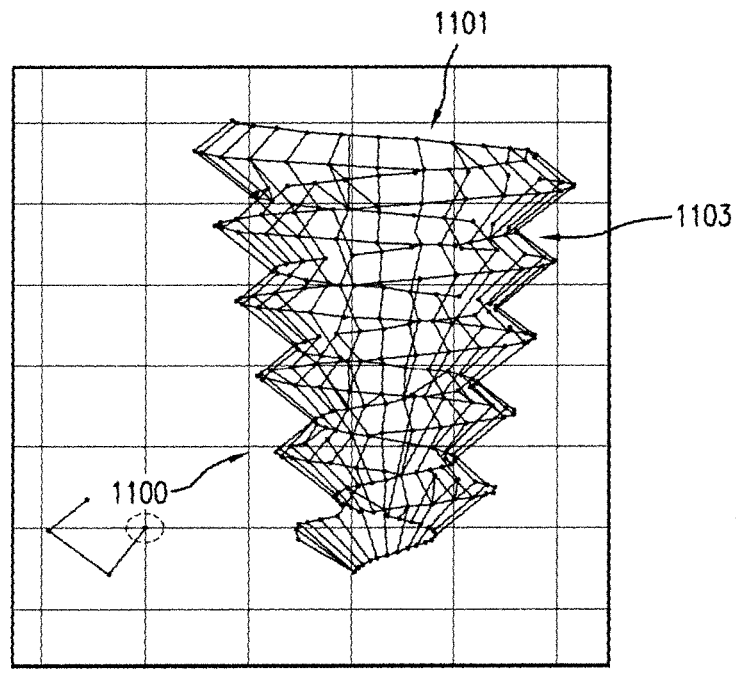
FIGS. 11A-11B shows another embodiment of a stent of the present invention.
Figure 11B:
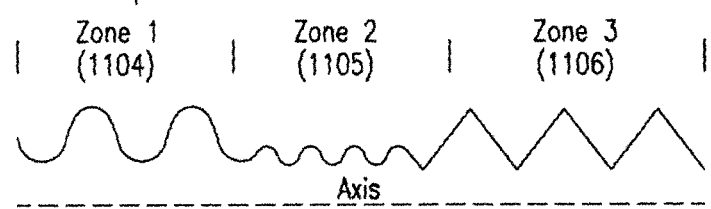

Referring now to FIGS. 11A-11B another embodiment of a stent 1100 has a larger proximal end 1101 with a helical surface channel 1103. The stent 1100 is in the shape of a cone or a cylinder with alternating variation in the diameter of the stent body. The surface channel 1103 may have regions 1104, 1105 and 1106 with different shapes and depth in each region, so as to change the flow rate, flow volume, and/or in each region.

Figure 12:
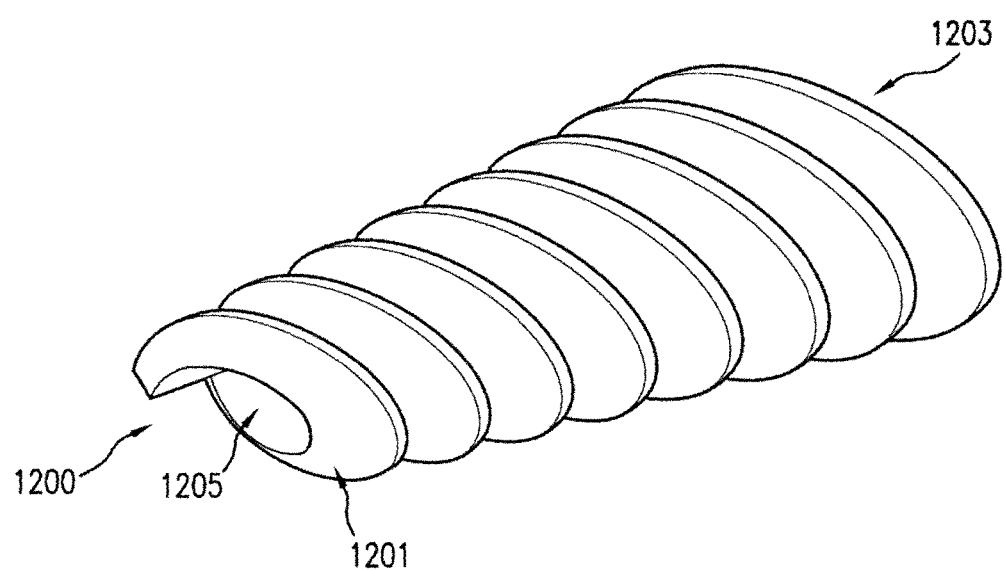
FIG. 12 shows another embodiment of a stent of the present invention.

FIG. 12 shows another embodiment of a stent 1200. The pitch of the stent can change in various zones of the stent. The stent has a smaller diameter in the proximal end 1201 and larger diameter in the distal end 1203. The stent 1200 may have an opening 1205 that is big enough to adapt a wire. The stent 1200 may have a gradual increasing or decreasing pitch. In another embodiment, the pitch may change in different sections of the stent to better contour to the anatomy.

Other embodiments of stents of the present invention are shown in FIGS. 15-18.

Figure 15:
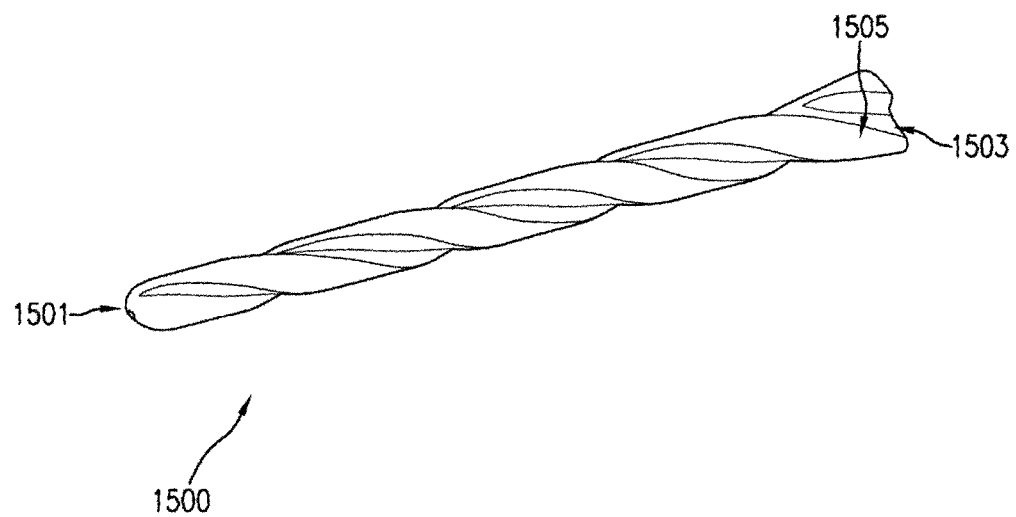
FIG. 15 shows another embodiment of a stent of the present invention.

FIG. 15 shows an embodiment of a stent 1500 with a conical tip 1501 to allow for ease of access into the area it will be placed, a flared distal end 1503 for anchoring or prevention of migration into a lumen, out of a lumen, or within a lumen. The flares 1505 can be unidirectional or bi directional.

Figure 16:
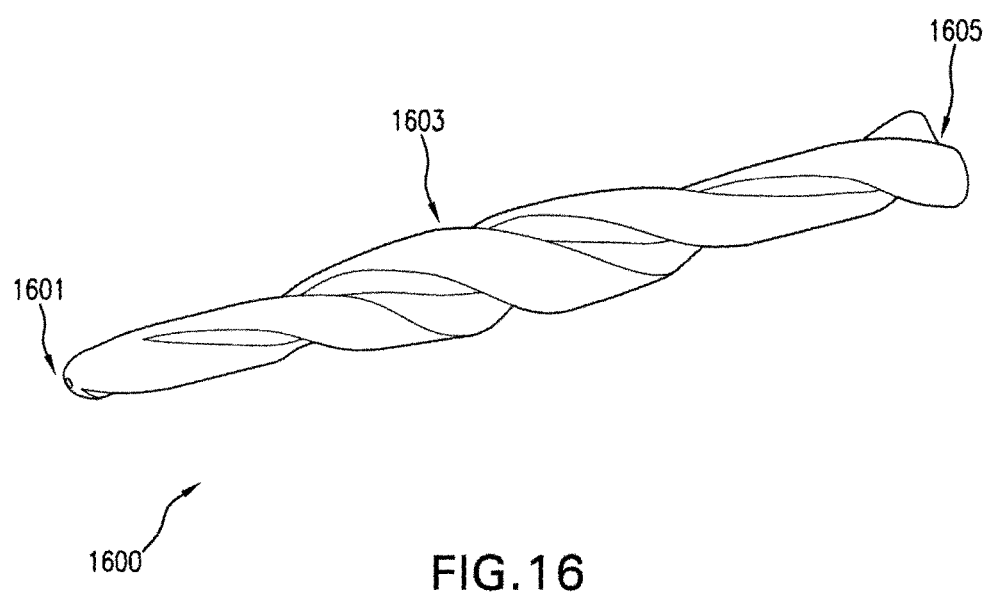
FIG. 16 shows another embodiment of a stent of the present invention.

FIG. 16 shows an embodiment of a stent 1600 with a conical end 1601 and a swollen middle section 1603. The stent 1600 may be made from an elastomer. In one embodiment, the elastomer may expands more in a area in the middle, the end, or in multiple locations of the stent body to increase fluid flow by providing larger and deeper channels in the stent. In another embodiment, the end of the stent 1600 has an anti migration mechanism that will expand to keep the stent in place. Anti migration device at the distal end 1605 of the stent can be located anywhere along the length of the stent access.

Figure 17:
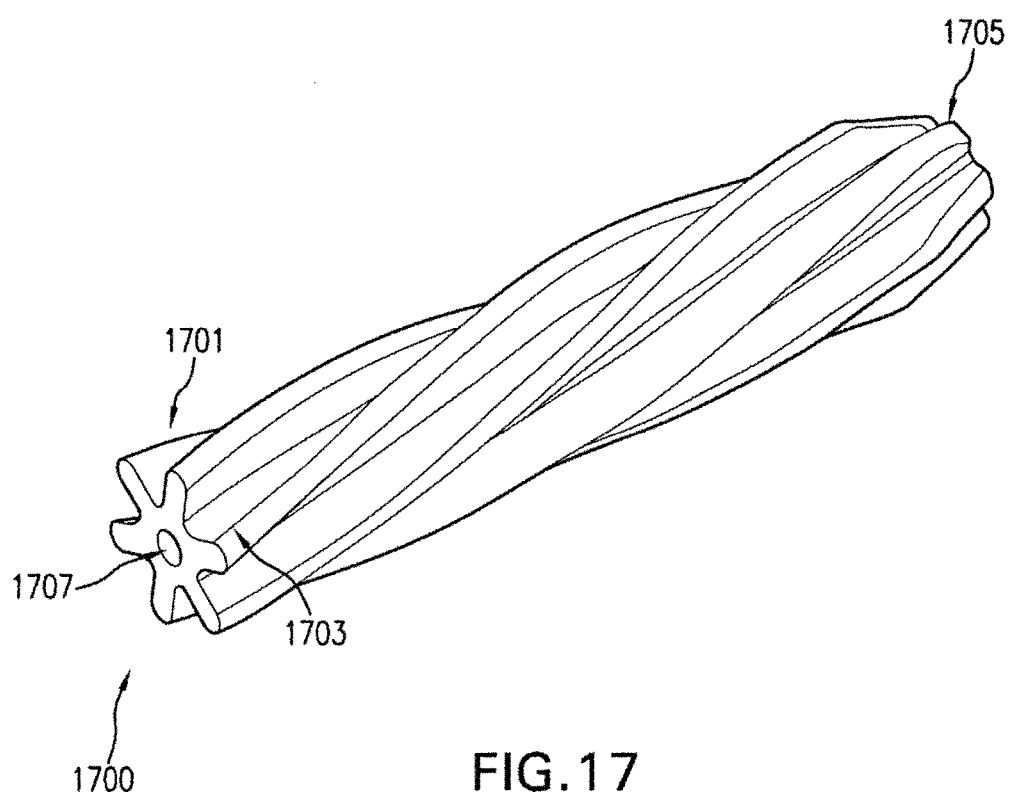
FIG. 17 shows another embodiment of a stent of the present invention.

FIG. 17 shows another embodiment of a stent 1700 with leaflets 1701 to form channels 1703. In this embodiment, the stent 1700 has a tapered end 1705 to allow for ease of entry. The rotation of the sinusoidal channels 1703 may be changed to adjust fluid flow, collapse ability, etc. The leaflets attached to the cam 1707 can be folded over to allow the diameter of the stent 1700 to become smaller when being loaded into a deliver device or being place in a deliver tube like an endoscope. The channels walls can be straight, rounded, or a combination thereof depending on the cavity or lumen where the stent is placed.

Figure 18:
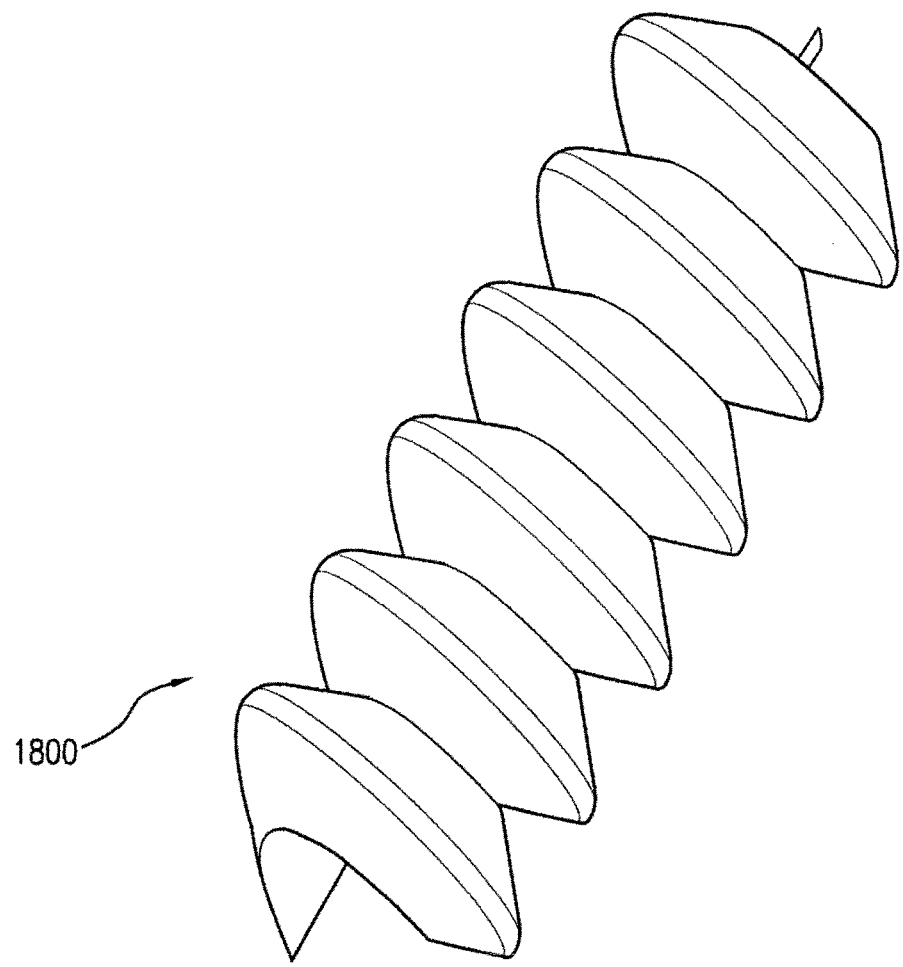
FIG. 18 shows another embodiment of a stent of the present invention.

FIG. 18 shows another embodiment of a stent 1800. The stent 1800 is made in a way to allow the sinusoidal channel of the stent occur on the inside of the stent. The outside of the stent conforms to the anatomy the stent is placed in and flexibility is determined by the pitch of the sinusoidal channel. The inside of the stent forms the same sinusoidal as the outside of the stent. In one embodiment, the stent 1800 is made in such a way that it can be inserted in a screw in fashion.

A person or ordinary skill in the art would understand that other folding or interlocking may also be employed. The channel walls or leaflets can also be of varying thicknesses and lengths to provide the stent with desired rigidity, flexibility, pushability, trackability, luminal contact and/or absorption profile. For example, a stent made from bioabsorable material may have leaflets that are thinner at the tip (where they touch the lumen wall) and thicker at the base (where they are attached to the cam), thus allowing for degradation from the tip to the base. In another embodiment, the cam itself can be cut in various ways to change its diameter at different points to change the pushability and flexibility of the device.

The present stent is typically made from a polymer material, plastics, metals, or alloys. Notable variations exist within each type. In certain embodiments, the stent is made from a non-polymer material. Examples of such materials include, but are not limited to, stainless steel, cobalt alloys such as cobalt-chromium, titanium alloys, tantalum, niobium, tungsten, molybdenum and nitinol. For example, self-expanding metal stents are generally made from nitinol, while some balloon-expandable metal stents are made from stainless steel. A coating, such as polyurethane coating, may be used to prevent non-polymer stent material from coming into direct contact with its surroundings. The coating slows down the rate of in-growth, allowing the stent to remain in the patient with a lower potential for side effects.

The stent may also be made with a bioabsorable material. Examples of bioabsorable materials include, but are not limited to, polylactic acid or polylactide (PLA), polyglycolic acid or polyglycolide (PGA), poly-.epsilon.-caprolactone (PCL), polyhydroxybutyrate (PHB), and co-polymers thereof.

In one embodiment, the bioabsorable material is degraded based on varying levels of pH. For example, the material may be stable at a neutral pH but degrades at a high pH. Examples of such materials include, but are not limited to chitin and chitosean. In another embodiment, the bioabsorable material is degradable by enzymes, such as lysozymes.

In another embodiment, the polymers include transparent plastic polymers, thermoplastic polyurethane or silicone polymers.

In another embodiment, the elongated body comprises a combination of a polymer and a non-polymer material.

In another related embodiment, the elongated stent body is made of a magnesium and chitin alloy.

In another related embodiment, the elongated stent body is made with a magnesium core coated with a chitin chitosan, N-acylchitosan hydrogel outer layer. The magnesium core may additionally include rare earth materials.

In another related embodiment, the elongated stent body is made of a chitin and chitosan, N-acylchitosan hydrogel and magnesium alloy with raw earth elements.

In another embodiment, the bioabsorable material may absorb moisture and expand in situ at the treatment site. For example, the stent made of Chitin or a variable copolymer of Chitin and PLGA or Chitin and Magnesium and other raw earth minerals would swell once it comes into contact with various body fluids. In one embodiment, the stent has a pre-implantation diameter Dpre (i.e., dry diameter) of 2.8 mm and is expandable to a post-implantation diameter Dpost, (i.e., wet diameter) of 3.3 mm after exposure to body liquid in a lumen. As used hereinafter, the "pre-implantation diameter Dpre" refers to the largest diameter of a stent body before implantation and the "post-implantation diameter Dpost" refers to the largest diameter of the stent body after implantation.

In another embodiment, the bioabsorable material is embedded with, or configured to carry, various agents or cells. The agents may be coupled to the outer and/or inner surfaces of stent body or integrated into the bioabsorable material itself. In one embodiment, the bioabsorable stent has a hollow center lumen so that agents may be placed inside the lumen to increase the dose release. The stent can additionally have multiple reservoirs, one inside the other, so that when the outer layer is absorbed the next reservoir is exposed and a further release of a larger dose of the chosen agents or cells. The chosen agent or cells may also be mixed with the polymer for sustained release.

Examples of agents that can be embedded into or carried by a stent include, but are not limited to, small molecule drugs, biologicals and gene transfer vectors. Examples of small molecule drugs include, but are not limited to, sirolumus, rapamycian, and other antiproliferating agent.

Examples of biologicals include, but are not limited to, antimicrobial agents and chemotherapeutic agents.

The term "antimicrobial agent" as used in the present invention means antibiotics, antiseptics, disinfectants and other synthetic moieties, and combinations thereof, that are soluble in organic solvents such as alcohols, ketones, ethers, aldehydes, acetonitrile, acetic acid, formic acid, methylene chloride and chloroform. Classes of antibiotics that can possibly be used include tetracyclines (i.e., minocycline), rifamycins (i.e., rifampin), macrolides (i.e., erythromycin), penicillins (i.e., nafcillin), cephalosporins (i.e., cefazolin), other beta-lactam antibiotics (imipenem, aztreonam), aminoglycosides (i.e., gentamicin), chloramphenicol, sulfonamides (i.e., sulfamethoxazole), glycopeptides (i.e., vancomycin), quinolones (i.e., ciprofloxacin), fusidic acid, trimethoprim, metronidazole, clindamycin, mupirocin, polyenes (i.e., amphotericin B), azoles (i.e., fluconazole) and beta-lactam inhibitors (i.e., sulbactarn).

Examples of specific antibiotics that can be used include minocycline, rifainpin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfiloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole and nystatin. Other examples of antibiotics, such as those listed in U.S. Pat. No. 4,642,104, herein incorporated by reference, will readily suggest themselves to those of ordinary skill in the art. Examples of antiseptics and disinfectants are thymol, a-terpineol, methylisothiazolone, cetylpyridinium, chloroxylenol, hexachlorophene, cationic biguanides (i.e., chlorhexidine, cyclohexidine), methylenechloride, iodine and iodophores (i.e., povidone-iodine), triclosan, firanmedical preparations (i.e., nitrofurantoin, nitrolurazone), methenamine, aldehydes (i.e., glutaraldehyde, formaldehyde) and alcohols. Other examples of antiseptics and disinfectants will readily suggest themselves to those of ordinary skill in the art.

The stent of the present invention may also be prepared with antimicrobial agents in other ways customary in the art. For example, the stent may be made in its entirety or in part of an antimicrobial polymer, or at least one surface of the stent may have embedded, by ion beam assisted deposition or co-extrusion techniques, therein with atoms of an antimicrobial polymer. Other suitable examples can be found in the art, for example, U.S. Pat. No. 5,520,664, which is incorporated herein by reference.

Chemotherapeutic agents can be coupled with the stent of the present invention in a manner analogous to that of antimicrobial agents. Exemplary chemotherapeutic agents include but are not limited to cis-platinum, paclitaxol, 5-flourouracial, gemcytobine and navelbine. The chemotherapeutic agents are generally grouped as DNA-interactive agents, antimetabolites, tubulin-interactive agents, hormonal agents, hormone-related agents, and others such as asparaginase or hydroxyurea. Each of the groups of chemotherapeutic agents can be further divided by type of activity or compound. The chemotherapeutic agents used in combination with the anti-cancer agents or benzimidazoles of this invention include members of all of these groups. For a detailed discussion of the chemotherapeutic agents and their method of administration, see Don, et al, Cancer Chemotherapy Handbook, 2d edition, pages 15-34, Appleton & Lange (Connecticut, 1994), herein incorporated by reference.

Examples of DNA-Interactive agents include, but are not limited to, alkylating agents, DNA strand-breakage agents; intercalating and nonintercalating topoisomerase II inhibitors, and DNA minor groove binders. Alkylating agents generally react with a nucleophilic atom in a cellular constituent, such as an amino, carboxyl, phosphate, or sulfhydryl group in nucleic acids, proteins, amino acids, or glutathione. Examples of alkylating agents include, but are not limited to, nitrogen mustards, such as chlorambucil, cyclophosphamide, isofamide, mechlorethainine, Melphalan, uracil mustard; aziridines, such as thiotepa; methanesulfonate esters such as busulfan; nitroso, ureas, such as cannustine, lomustine, streptozocin; platinum complexes, such as cisplatin, carboplatin; bioreductive alkylator, such as mitomycin, and procarbazine, dacarbazine and altretamine. DNA strand breaking agents include, but are not limited to, bleomycin. Intercalating DNA topoisomerase II inhibitors include, but are not limited to, intercalators such as amsacrine, dactinomycin, daunorubicin, doxorubicin, idarubicin, and mitoxantrone.

Nonintercalating DNA topoisomerase II inhibitors include, but are not limited to etoposide and teniposide. DNA minor groove binders include, but are not limited to, plicamycin.

Antimetabolites interfere with the production of nucleic acids by one or the other of two major mechanisms. Some of the drugs inhibit production of the deoxyribonucleoside triphosphates that are immediate precursors for DNA synthesis, thus inhibiting DNA replication. Some of the compounds, for example, purines or pyrimidines, are sufficient to be able to substitute for them in the anabolic nucleotide pathways. These analogs can then be substituted into the DNA and RNA instead of their normal counterparts. The antimetabolites useful herein include: folate antagonists such as methotrexate and trimetrexate pyrimidine antagonists, such as fluorouracil, fluorodeoxyuridine, CB3717, azacytidine, cytarabine, and floxuridine purine antagonists include mercaptopurine, 6-thioguanine, fludarabine, pentostatin; sugar modified analogs include cyctrabine, fludarabine; ribonucleotide reductase inhibitors include hydroxyurea. Tubulin interactive agents act by binding to specific sites on tubulin, a protein that polymerizes to form cellular microtubules. Microtubules are critical cell structure units. When the interactive agents bind on the protein, the cell cannot form microtubules tubulin interactive agents including vincristine and vinblastine, both alkaloids and paclitaxel.

Hormonal agents are also useful in the treatment of cancers and tumors. They are used in hormonally susceptible tumors and are usually derived from natural sources. These include: estrogens, conjugated estrogens and ethinyl estradiol and diethylstilbestrol, chlorotrianisene and idenestrol; progestins such as hydroxyprogesterone caproate, medroxyprogesterone, and megestrol; androgens such as testosterone, testosterone propionate; fluoxymesterone, metbyltestosterone; adrenal corticosteroids are derived from natural adrenal cortisol or hydrocortisone. They are used because of their anti-inflammatory benefits as well as the ability of some to inhibit mitotic divisions and to halt DNA synthesis. These compounds include prednisone, dexamethasone, methylprednisolone, and prednisolone.

Hormone-related agents include, but are not limited to, leutinizing hormone releasing hormone agents, gonadotropin-releasing hormone antagonists and anti-hormonal agents. Gonadotropin-releasing hormone antagonists include leuprolide acetate and goserelin acetate. They prevent the biosynthesis of steroids in the testes and are used primarily for the treatment of prostate cancer.

Antihormonal agents include antiestrogenic agents such as tamosifen, antiandrogen agents such as Flutamide; and antiadrenal agents such as mitotane and aminoglutethimide. Hydroxyurea appears to act primarily through inhibition of the enzyme ribonucleotide reductase. Asparaginase is an enzyme that converts asparagine to nonfunctional aspartic acid and thus blocks protein synthesis in the tumor.

Gene transfer vectors are capable of introducing a polynucleotide into a cell. The polynucleotide may contain the coding sequence of a protein or a peptide, or a nucleotide sequence that encodes a iRNA or antisense RNA. Examples of gene transfer vectors include, but are not limited to, non-viral vectors and viral vectors. Non-viral vectors typically include a plasmid having a circular double stranded DNA into which additional DNA segments can be introduced. The non-viral vector may be in the form of naked DNA, polycationic condensed DNA linked or unlinked to inactivated virus, ligand linked DNA, and liposome-DNA conjugates. Viral vectors include, but are not limited to, retrovirus, adenovirus, adeno-associated virus (AAV), herpesvirus, and alphavirus vectors. The viral vectors can also be astrovirus, coronavirus, orthomyxovirus, papovavirus, paramyxovirus, parvovirus, picornavirus, poxvirus, or togavirus vectors.

The non-viral and viral vectors also include one or more regulatory sequences operably linked to the polynucleotide being expressed. A nucleotide sequence is "operably linked" to another nucleotide sequence if the two sequences are placed into a functional relationship. For example, a coding sequence is operably linked to a 5' regulatory sequence if the 5' regulatory sequence can initiate transcription of the coding sequence in an in vitro transcription/translation system or in a host cell. "Operably linked" does not require that the DNA sequences being linked are contiguous to each other. Intervening sequences may exist between two operably linked sequences.

In one embodiment, the gene transfer vector encodes a short interfering RNA (siRNA). siRNAs are dsRNAs having 19-25 nucleotides. siRNAs can be produced endogenously by degradation of longer dsRNA molecules by an RNase III-related nuclease called Dicer. siRNAs can also be introduced into a cell exogenously or by transcription of an expression construct. Once formed, the siRNAs assemble with protein components into endoribonuclease-containing complexes known as RNA-induced silencing complexes (RISCs). An ATP-generated unwinding of the siRNA activates the RISCs, which in turn target the complementary mRNA transcript by Watson-Crick base-pairing, thereby cleaving and destroying the mRNA. Cleavage of the mRNA takes place near the middle of the region bound by the siRNA strand. This sequence specific mRNA degradation results in gene silencing. In another embodiment, the gene transfer vector encodes an aiitisense RNA.

Examples of cells include, but are not limited to, stem cells or other harvested cells.

Manufacture of Stent

The stent body and surface channels can be laser cut, water jet cut, extruded, stamped, molded, laythed or formed. In one embodiment, the stent is cut from a single polymer tube that may be extruded. The tube may be hollow or the center may be cored out at varying diameters suitable for the particular indication.

The stent is then etched and is formed on a suitable shaping device to give the stent the desired external geometry. Both the synthetic collar techniques and in vitro valuation techniques show the remarkable ability of stents of the present invention to convert acting force into deformation work absorbed by the angled structure, which prevents excessive scaffolding stress, premature material fatigue and accelerated obsolescence.

The stent of the present invention may be formed in such a way as to allow fluid flow to change in the pitch of the flow to improve flow dynamics and to speed the flow of fluids throughout the device. From a tight radial design to a more longitudinal design.

In one embodiment spiral surface channels with large cross-section areas are formed to accommodate large volumes of body fluid. In another embodiment, multiple channels with small cross-section area are formed to accommodate large volumes of body fluid. In another embodiment, the stent body contains a large center lumen to allow for fluid flow and a plurality of small cross-section area channels on the surface to stabilize the stent in vivo.

In another embodiment, the lips of the channel walls are taped to increase the surface area for fluid flow and grip. Changes in the depth of the pitch of the channels will also have an impact on fluid flow and stability.

In one embodiment, the stent is formed on a shaping tool that has substantially the desired contour of the external stent dimensions. In the event the stent is to be shaped to the dimensions of a particular lumen, optical photography and/or optical videography of the target lumen may be conducted prior to stent formation. The geometry of corresponding zones and connector regions of the stent then can be etched and formed in accordance with the requirements of that target lumen. In particular, if the topography of the biliary duct of a particular patient is captured optically and the appropriate dimension provided, a patient specific prosthesis can be engineered. These techniques can be adapted to other non-vascular lumens but is very well suited for vascular applications where patient specific topography is a function of a variety of factors such as genetics, lifestyle, etc.

Unlike stents made from shape memory metals, the stents of the present invention can take on an infinite number of characteristic combinations as zones and segments within a zone can be modified by changing angles, segment lengths, segment thicknesses, pitch during the etching and forming stages of stent engineering or during post formation processing and polishing steps. Moreover, by modifying the geometry, depth, and diameter of the channels between zones, additional functionality may be achieved, such as flexibility, increased fluid transport, and changes in friction.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A stent comprising:
an elongated body having a proximal end, a distal end, a central axis, and at least one open sinusoidally undulating channel helically and longitudinally wound around said central axis, wherein said undulating channel is formed on an exterior surface of said elongated body to provide fluid communication between said proximal end and said distal end,
wherein said elongated body is made from a non-polymer material selected from the group consisting of stainless steel, cobalt alloys, titanium alloys, tantalum, niobium, tungsten and molybdenum and wherein said elongated body further comprises a center lumen that is not in fluid communication with said undulating channel.

2. The stent of claim 1, wherein said elongated body comprises a plurality of sinusoidally undulating channels helically and longitudinally wound around said central axis, wherein said undulating channels are formed on the exterior surface of said elongated body.

3. The stent of claim 1, wherein said distal end and said proximal end have different diameters.

4. The stent of claim 1, wherein said elongated body has a sinusoidal shape.

5. The stent of claim 1, wherein said body further comprises an anchoring device.

6. The stent of claim 1, wherein said elongated body further comprises a biological agent.

7. The stent of claim 6, wherein said biological agent is selected from the group consisting of chemotherapeutic agents, antimicrobial agents and gene transfer agents.

8. The stent of claim 1, wherein said channel is formed by compressible channel walls that can be compressed against each other in a compressed state to reduce the diameter of said stent.

9. The stent of claim 1, wherein said stent has a pre-implantation diameter $D_{pre}$ and is in situ expandable upon absorption of a body fluid to a post-implantation diameter $D_{post}$ wherein $D_{post}$ is greater than $D_{pre}$.

10. A stent comprising:
an elongated body having a proximal end, a distal end, at least one open sinusoidally undulating channel formed on an exterior surface of said elongated body to provide fluid communication between said proximal end and said distal end, and a center lumen that is not in fluid communication with said undulating channel,
wherein said elongated body is made from a combination of polymer and non-polymer material selected from the group consisting of stainless steel, cobalt alloys, titanium alloys, tantalum, niobium, tungsten and molybdenum.

* * * * *